(12) United States Patent
Yuan et al.

(10) Patent No.: US 11,168,294 B2
(45) Date of Patent: Nov. 9, 2021

(54) THREE-DIMENSIONAL CELL CULTURE SCAFFOLD AND PREPARATION METHOD THEREOF

(71) Applicant: Guangzhou Jet Bio-Filtration Co., Ltd., Guangzhou (CN)

(72) Inventors: Jianhua Yuan, Guangzhou (CN); Jialiang Su, Guangzhou (CN); Yong Chen, Guangzhou (CN)

(73) Assignee: GUANGZHOU JET BIO-FILTRATION CO., LTD., Guangzhou (CN)

( * ) Notice: Subject to any disclaimer, the term of this patent is extended or adjusted under 35 U.S.C. 154(b) by 492 days.

(21) Appl. No.: 15/775,678

(22) PCT Filed: Jan. 29, 2016

(86) PCT No.: PCT/CN2016/072756
§ 371 (c)(1),
(2) Date: Jul. 24, 2018

(87) PCT Pub. No.: WO2017/080117
PCT Pub. Date: May 18, 2017

(65) Prior Publication Data
US 2018/0362911 A1    Dec. 20, 2018

(30) Foreign Application Priority Data
Nov. 13, 2015  (CN) .......................... 201510783345.3

(51) Int. Cl.
C12M 1/12    (2006.01)
C12N 5/00    (2006.01)
B33Y 10/00   (2015.01)

(52) U.S. Cl.
CPC ............. *C12M 25/14* (2013.01); *B33Y 10/00* (2014.12); *C12N 5/0062* (2013.01); *C12N 2533/40* (2013.01)

(58) Field of Classification Search
None
See application file for complete search history.

(56) References Cited

U.S. PATENT DOCUMENTS

| 2003/0180942 A1* | 9/2003 | Van Der Merwe .... C12M 23/20 435/299.1 |
| 2008/0026464 A1* | 1/2008 | Borenstein .......... A61L 27/3886 435/395 |

FOREIGN PATENT DOCUMENTS

| CN | 1455812 A | 11/2003 |
| CN | 101245313 A | 8/2008 |
| CN | 104667344 A | 6/2015 |
| CN | 104830774 A | 8/2015 |
| CN | 105238735 A | 1/2016 |
| CN | 205077067 A | 3/2016 |
| WO | 2017080116 A1 | 5/2017 |

OTHER PUBLICATIONS

Lee et al. "Three-dimensional cell culture matrices: state of the art." Tissue Engineering Part B: Reviews 14.1 (2008): 61-86. (Year: 2008).*
Loh et al. "Three-dimensional scaffolds for tissue engineering applications: role of porosity and pore size." Tissue Engineering Part B: Reviews 19.6 (2013): 485-502. (Year: 2013).*
Bhushan et al. "A review of block copolymer-based biomaterials that control protein and cell interactions." Journal of Biomedical Materials Research Part A 102.7 (2014): 2467-2480. (Year: 2014).*
Costa et al. "Effect of butadiene/styrene ratio, block structure and carbon nanotube content on the mechanical and electrical properties of thermoplastic elastomers after UV ageing." Polymer Testing 42 (Feb. 13, 2015): 225-233. (Year: 2015).*
Wang et al., "Cell scaffolds prepared by 3D printing technology to construct a three-dimensional model of lung cancer in vitro", Huadong Thoracic Oneology Symposium, 2014, and English Abstract (6 pages). This article is listed on First Search Report of CN201510783345.3, which was cited in the IDS filed on May 11, 2018.
Shi et al., "Preparation of Porous cell Scaffolds of Poly(L-lactic acid) and Poly(L-lactic-co-glycolic acid) and the Measurement of their Porosities", Journal of Functional Polymers: DOI 10. 14133, vol. 14, Mar. 2001, and English Abstract (5 pages). This article is listed on First Search Report of CN201510783345.3, which was cited in the IDS filed on May 11, 2018.
Unpublished U.S. Appl. No. 15/775,695, filed May 11, 2018.
English Translation of International Search Report thereof for International Application No. PCT/CN2016/072756, dated Jul. 27, 2016 (3 pages).
Lee, J. et al., "Three-Dimensional Cell Culture Matrices: State of the Art." Tissue Engineering: Part B., vol. 14, No. 1, Dec. 31, 2008 (pp. 61-86).
First Search Report of CN201510783345.3 (1 page).

* cited by examiner

*Primary Examiner* — Emily A Cordas
(74) *Attorney, Agent, or Firm* — Kagan Binder, PLLC

(57) ABSTRACT

A three-dimensional cell culture scaffold and preparation method thereof. The preparation method comprises the following steps: designing, according to a shape of a cell culture device, a shape of the three-dimensional cell culture scaffold; printing once by a 3D printer to form the three-dimensional cell culture scaffold; performing a surface treatment, by a surface treating agent, on the three-dimensional cell culture scaffold manufactured by 3D printing to obtain a resultant three-dimensional cell culture scaffold. By adopting a three-dimensional printing technology to manufacture a three-dimensional fibrous cell culture scaffold having a three-dimensional fibrous network structure, raw materials and a manufacturing time can be saved, reducing production costs, increasing production efficiency, decreasing power consumption, preventing a flaw in the conventional manufacturing technique, and facilitating large-scale intelligent manufacturing.

4 Claims, No Drawings

THREE-DIMENSIONAL CELL CULTURE SCAFFOLD AND PREPARATION METHOD THEREOF

TECHNICAL FIELD

The present disclosure relates to cell culture technical field, in particular to a three-dimensional cell culture scaffold and preparation method thereof.

BACKGROUND

In recent years, technologies in the pharmaceutical industry, life sciences, medicine, clinical quarantine and inspection, cell therapy and tissue engineering industry have developed rapidly. Currently, expression of specific proteins, monoclonal antibodies, interferons and viruses, vaccine products, and cell therapy products by in vitro large-scale culture of animal cells has become a key focus area of research and application. So far, the commonly used large-scale cell culture devices include cell culture dishes, multi-well culture plates, culture flasks, culture roller bottles, bioreactors, and cell factories. Cells mostly grow adherently to the wall and proliferate in the culture environment in a two-dimensional plane manner.

Although the two-dimensional planar cell culture satisfies, to some extent, the development needs of the cell culture industry, it has many defects such as easy occurrence of crowding phenomenon for cells cultured in such environment resulting in contact inhibition of cells, reduced superficial area of cells exposed to culture medium, and limited attached superficial area of cells. Two-dimensional cell culture lacks the interactions between cells and cells and between cells and extracellular matrix as in in vivo three-dimensional environment, thereby limiting the proliferation of cells, which is not conducive to their differentiation and expression of the original functions. Therefore, three-dimensional cell culture came into being. Three-dimensional cell culture means that cells are first seeded on a culture carrier with a three-dimensional network space structure, and then on this three-dimensional carrier, the cells attach, migrate, and differentiate and proliferate. Three-dimensional cell culture overcomes many of the defects in two-dimensional planar culture. The three-dimensional network space structure may provide a larger surface area for cell adhesion, increase cell yield while reducing or even avoiding contact inhibition of cells, provide a three-dimensional microenvironment for cell growth similar to human body, facilitate the interactions between cells and between cells and extracellular matrix and the excretion of metabolites, and ensure that the cells maintain their original differentiation and functional expression.

In most of three-dimensional cell culture systems currently used, natural polymers such as collagen, polypeptide, gelatin, fibrin, agarose syrup, alginate and the like are used as scaffold material for cell adhesion, the particular steps are as follows: first making the natural polymer material into a hydrogel, and then mixing the cells with other nutrients such as the hydrogel and culture medium to form a three-dimensional cell culture system in a hydrogel state. Although this kind of three-dimensional culture system has been improved relatively obviously compared to two-dimensional culture, there are still many defects. Since the whole culture system is in gel state with a relatively large viscosity, it is unfavorable for not only transport of nutrients to cells located deep in the scaffold, but also the excretion of cellular metabolites. In addition, this kind of culture system is also not helpful for separation of the cells from the scaffold which attached, resulting in difficulties in harvesting cells and recycling scaffold materials. Most of the three-dimensional culture systems in gel state are also difficult to use for dynamic observation for the cultured cells at any time. Therefore, there is an urgent need for a new three-dimensional cell culture system capable of overcoming the above-mentioned defects.

The polystyrene fiber porous scaffold prepared by Baker et al. using electrospinning technology can be placed into a multi-well plate as a three-dimensional cell culture insert. However, the size of fibers in the three-dimensional fiber cell culture insert is difficult to control, the pore size and shape of the three-dimensional fibers are indeterminate and non-uniform, the average pore size is small (about 15 μm), moreover, the three-dimensional scaffold is soft in the state of nature, resulting in that the overall shape of the three-dimensional insert cannot be maintained. Therefore, the above mentioned polystyrene fiber porous scaffold still has many defects as a three-dimensional cell culture insert. Qing Liu disclosed a method for manufacturing a three-dimensional fiber cell culture insert by firstly using a process of injection molding or the like to produce a single-layer porous sheet scaffold, and then performing layer-by-layer assembly by means of pillars or bonding, etc. Although, this resultant three-dimensional fiber cell culture insert overcomes many of the defects in other existing three-dimensional cell culture systems, this method has complex preparation process, high energy consumption, high production cost and difficulty in large-scale preparation.

SUMMARY OF THE INVENTION

Based on this, an object of the present disclosure is to provide a new method of preparing a three-dimensional cell culture scaffold.

The detailed technical solution is as follows:

A method of preparing a three-dimensional cell culture scaffold comprising:

designing, according to a shape of a cell culture device, a shape of the three-dimensional cell culture scaffold;

printing once by a 3D printer to form the three-dimensional cell culture scaffold;

performing a surface treatment, by a treating agent, on a surface of the three-dimensional cell culture scaffold manufactured by the 3D printing to obtain a resultant three-dimensional cell culture scaffold.

In some embodiments, the raw material used for the 3D printer is a non-biodegradable polymer selected from one or more of the group consisting of polystyrene, polypropylene, polyethylene, polycarbonate, and copolymers thereof, or a biodegradable polymer selected from one or more of the group consisting of polylactic acid, polylactide-glycolate, polycaprolactone, and copolymers thereof.

In some embodiments, the raw material used for the 3D printer is a composite of transparent polystyrene and transparent styrene-butadiene random copolymer in a mass ratio of 0-90:100-10.

In some embodiments, transparent polystyrene and transparent styrene-butadiene random copolymer in the blend is in a mass ratio of 90-60:10-40; styrene and butadiene in the transparent styrene-butadiene random copolymer is in a molar ratio of 90-50:10-50.

In some embodiments, the treating agent is selected from the group consisting of a plasma hydrophilic treating agent and a temperature sensitive treating agent.

In some embodiments, the plasma hydrophilic treating agent is selected from the group consisting of an oxygen gas, a nitrogen gas, a carbon dioxide, a carboxylic acid or a derivative thereof (such as saturated or unsaturated small-molecular aliphatic carboxylic acids or aromatic carboxylic acids with a molecular weight less than 500), and amino acids or derivatives thereof with a molecular weight of less than 500.

In some embodiments, the temperature sensitive treating agent is N-isopropyl acrylamide or a derivative thereof.

In some embodiments, the cell culture device is selected from the group consisting of a cell culture dish, a cell culture flask, a multi-well cell culture plate, a cell culture roller bottle, a cell culture tube, and a bioreactor.

Process technology method for assembling the three-dimensional fiber cell culture scaffold into a cell culture device is as follows: for non-enclosed cell culture devices such as culture dishes, multi-well culture plates and the like, placing the three-dimensional fiber cell culture scaffold directly inside the cell culture device, then seeding and culturing cells; and for enclosed cell culture devices such as culture flasks, culture roller bottles and the like, placing the three-dimensional fiber cell culture scaffold into a cell culture device opened in one side, then sealing the missing side of the cell culture device by welding process such as ultrasonic welding, thermal welding, laser sintering welding and the like, finally seeding and culturing cells.

Another object of the present disclosure is to provide a three-dimensional cell culture scaffold.

The particular technical solution is as follows:

A three-dimensional cell culture scaffold is prepared by the above mentioned method.

In some embodiments, parameters for a three-dimensional fiber network structure of the three-dimensional cell culture scaffold are as follows: a fiber diameter is 30-1,000 μm, a spacing between adjacent fibers is 50-1,500 μm, a number of parallel planar layers is 1-100,000, and a spacing between adjacent planar layers is 30-1,000 μm.

The interior of the three-dimensional fiber cell culture scaffold may have a hollow channel of a cylindrical shape, a rectangular parallelepiped shape, or various prismatic shapes. The circumscribed cylinder of the hollow channel has a diameter of 300-5,000 μm.

The principle and advantages of the present disclosure are as follows:

3D printing technology has been developing since the end of the 19th century. However, the golden era of 3D printing technology has just come in recent years, owing to the continuous advancement of information technology, the continuous updating of machine automation and the promotion of the Internet. 3D printing technology is called "the third industrial revolution" and belongs to the field of intelligent additive manufacturing. The manufacturing process of 3D printing is first designing and processing a 3D graphic for the product, then converting it into a data format which can be identified by a 3D printer, and then importing it into the 3D printing system for 3D printing. There is no need to design, manufacture, and modify molds for a product with complex structures such as cavities or movable parts inside, so the products can be rapidly printed out and formed once. Therefore, by adopting the three-dimensional printing technology to manufacture a three-dimensional fiber cell culture scaffold having a three-dimensional fiber network structure, there would be simplified manufacture process, economical raw material and manufacture time, reduced production cost, vastly improved production efficiency, decreased power consumption, avoided traditional manufacturing technology defects, and convenience for large-scale intelligent manufacturing.

In the present disclosure, it is preferable to use a complex of transparent polystyrene and transparent styrene-butadiene random copolymer in a mass ratio of 0-90:100-10 as material of three-dimensional cell culture scaffold. The transparent polystyrene is selected from one or more of the group consisting of GPPS-1050 (Total), GPPS-1240 (Total), GPPS-535N (Total), PS Bycolene® 143E (BASF-YPC), PS Bycolene® 158K (BASF-YPC) and PS Bycolene® 165H (BASF-YPC), and the transparent styrene-butadiene random copolymer is selected from one or more of the group consisting of KR03 (Chevron Phillips), KR03NW (Chevron Phillips), BK10 (Chevron Phillips), SL-801G (Maoming Zhonghe), SL-803G (Maoming Zhonghe), SL-805F (Maoming Zhonghe) and SL-838F (Maoming Zhonghe). The material has advantages of high strength, high flexibility, free bending, high transparency, good fluidity, and not blocking nozzle of the printer, and is particularly suitable for biological fields with high requirements for transparency.

DETAILED DESCRIPTION OF THE PREFERRED EMBODIMENTS

The present disclosure will be described in detail below with reference to specific embodiments. The illustrated embodiments are merely a part of the embodiments of the present disclosure, rather than all the embodiments, and are merely used for illustrating the present disclosure, rather than limiting the scope of the present disclosure. Other embodiments obtained by those skilled in the art without any creative work fall within the protection scope of the present disclosure.

Example 1

According to the size of a 3.5 mm culture dish, a model of a three-dimensional fiber cell culture insert with a fiber diameter of 300 μm, a spacing between fibers in the same planar layer of 300 μm, a spacing between layers of 300 μm, and a layer number of 12 was designed using AutoCAD software. Then, 3D data of the model was converted to a 3D printing code, which was then input into a 3D printer. Using the 3D printer based on FDM principle, the designed three-dimensional fiber cell culture insert was printed out layer by layer with polypropylene (PP) linear material which has a diameter of 3 mm served as a raw material, under the condition of a print head temperature of 210° C. and a print linear speed of 30 mm/min. Using low temperature plasma technology, acrylic acid graft polymerization surface treatment was performed on the fiber surfaces in the three-dimensional fiber cell culture insert, followed by radiation sterilization using gamma rays. Then, the three-dimensional fiber cell culture insert was placed into a 3.5 mm diameter culture dish on a biological experiment table, followed by seeding and culturing the cells for 48 h, and finally the cells were harvested by trypsinization.

Example 2

According to the size of a 50 ml culture flask, a model of a three-dimensional fiber cell culture insert with a fiber diameter of 500 μm, a spacing between fibers in the same planar layer of 1,000 μm, a spacing between layers of 500 μm, and a layer number of 150 was designed using AutoCAD software. Then, a 3D data of the model was converted to a 3D printing code, which was then input into a 3D printer.

Using the 3D printer based on FDM principle, the designed three-dimensional fiber cell culture insert was printed out layer by layer with polystyrene (PS) linear material is which has a diameter of 1.75 mm served as a raw material, under the condition of a print head temperature of 240° C. and a print linear speed of 50 mm/min. Graft polymerization temperature sensitive surface treatment was performed with N-isopropyl acrylamide on the fiber surfaces in the three-dimensional fiber cell culture insert, followed by placing the treated three-dimensional fiber cell culture insert into a 50 ml culture flask opened on a side, then the culture insert was mounted inside the culture flask by ultrasound welding, followed by radiation sterilization using gamma rays. After that, the cells were seeded and cultured for 48 h, and finally the temperature of the system was lowered to 20° C. for temperature-sensitive treatment to harvest the cells.

Example 3

According to the size of a 850 ml culture flask, a model of a three-dimensional fiber cell culture insert with a fiber diameter of 1,000 μm, a spacing between fibers in the same planar layer of 2,000 μm, a spacing between layers of 1,000 μm, and a layer number of 1,500 was designed using AutoCAD software. Then, a 3D data of the model was converted to a 3D printing code, which was then input into a 3D printer. Using the 3D printer based on FDM principle, the designed three-dimensional fiber cell culture insert was printed out layer by layer with polyethylene (PE) linear material which has a diameter of 1.75 mm served as a raw material, under the condition of a print head temperature of 190° C. and a print linear speed of 80 mm/min. Graft polymerization temperature sensitive surface treatment was performed with N-isopropyl acrylamide on the fiber surfaces in the three-dimensional fiber cell culture insert, followed by placing the treated three-dimensional fiber cell culture insert into a 850 ml culture flask opened on a side, and then the culture insert was mounted inside the culture flask by ultrasound welding, followed by radiation sterilization using gamma rays. After that, the cells were seeded and cultured for 48 h, and finally the temperature of the system was lowered to 20° C. for temperature-sensitive treatment to harvest the cells.

Example 4

According to the size of a 2,000 ml culture roller bottle, a model of a three-dimensional fiber cell culture insert with a fiber diameter of 600 μm, a spacing between fibers in the same planar layer of 1,000 μm, a spacing between layers of 600 μm, and a layer number of 4,000 was designed using AutoCAD software. Then, a 3D data of the model was converted to a 3D printing code, which was then input into a 3D printer. Using the 3D printer based on FDM principle, the designed three-dimensional fiber cell culture insert was printed out layer by layer with polystyrene (PS) linear material which has a diameter of 1.75 mm served as a raw material, under the condition of a print head temperature of 240° C. and a print linear speed of 50 mm/min. Graft polymerization temperature sensitive surface treatment was performed with N-isopropyl acrylamide on the fiber surfaces in the three-dimensional fiber cell culture insert, followed by placing the treated three-dimensional fiber cell culture insert into a 50 ml culture flask opened on a side, and then the culture insert was mounted inside the culture flask by ultrasound welding, followed by radiation sterilization using gamma rays. After that, the cells were seeded and cultured for 48 h, and finally the temperature of the system was lowered to 20° C. for temperature-sensitive treatment to harvest the cells.

Example 5

10 kg polystyrene GPPS-1240 (Total) and 2.5 kg K resin (transparent styrene-butadiene random copolymer in which butadiene has a molar content of 30%) SL-803G (Maoming Zhonghe) were accurately weighed by a balance, then dried at 80° C. followed by predispersion blending. The predispersion blend was further subjected to melt blending at 230° C. for 6 minutes in a twin-screw blending extrusion apparatus, then extruded from a circular die with a diameter of 1.75 mm. The extruded wire rod was cooled and set by a cooling tank, hauled by a two-wheel tractor, and winded at a high speed of 30 m/min on a duplex winder and finally dried to obtain a transparent polystyrene linear material.

According to the size of a 2,000 ml culture roller bottle, a model of a three-dimensional fiber cell culture insert with a fiber diameter of 600 μm, a spacing between fibers in the same planar layer of 1,000 μm, a spacing between layers of 600 μm, and a layer number of 4,000 was designed using AutoCAD software. Then, a 3D data of the model was converted to a 3D printing code, which was then input into a 3D printer. Using the 3D printer based on FDM principle, the designed three-dimensional fiber cell culture insert was printed out layer by layer with transparent polystyrene linear material with a diameter of 1.75 mm prepared by above method served as a raw material, under the condition of a print head temperature of 240° C. and a print linear speed of 50 mm/min. Graft polymerization temperature sensitive surface treatment was performed with N-isopropyl acrylamide on the fiber surfaces in the three-dimensional fiber cell culture insert, followed by placing the treated three-dimensional fiber cell culture insert into a perfusion bioreactor. After sterilizing, the cells were seeded and perfusion-cultured for 48 h, and finally the temperature of the system was lowered to 20° C. for temperature-sensitive treatment to harvest the cells. Then, the cells were seeded to passage on the three-dimensional insert in the bioreactor, cultured circularly, and harvested circularly without being damaged.

The technical features of the above-described embodiments may be combined arbitrarily. To make the description brief, all the possible combinations of the technical features in the above embodiments have not been described. However, the combination of these technical features should be considered as falling within the scope described in this specification so long as there is no contradiction.

The above-mentioned embodiments merely represent several embodiments of the present disclosure, and the description thereof is comparatively specific and detailed, but it should not be construed as limiting the scope of the disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

What is claimed is:
1. A method of preparing a three-dimensional cell culture scaffold comprising:
designing, according to a shape of a cell culture device, a shape of the three-dimensional cell culture scaffold;
printing once by a three-dimensional (3D) printer to form the three-dimensional cell culture scaffold; and performing a surface treatment, by a treating agent, on a surface of the three-dimensional cell culture scaffold manufactured by the 3D printing, to obtain a resultant three-dimensional cell culture scaffold;

wherein a raw material used in the printing of the formed three-dimensional tissue scaffold by the 3D printer is a blend of transparent polystyrene and transparent styrene-butadiene random copolymer, and wherein the transparent polystyrene and the transparent styrene-butadiene random copolymer in the blend is in a mass ratio of 90-60:10-40; and wherein the treating agent is a plasma hydrophilic treating agent.

2. The method of claim 1, wherein the styrene and butadiene in the transparent styrene-butadiene random copolymer is in a molar ratio of 90-50:10-50.

3. The method of claim 1, wherein the plasma hydrophilic treating agent is selected from the group consisting of an oxygen gas, a nitrogen gas, a carbon dioxide, a carboxylic acid, and an amino acid.

4. The method of claim 1, wherein the cell culture device is selected from the group consisting of a cell culture dish, a cell culture flask, a multi-well cell culture plate, a cell culture roller bottle, a cell culture tube, and a bioreactor.

* * * * *